United States Patent
Addison et al.

(10) Patent No.: US 10,143,771 B2
(45) Date of Patent: Dec. 4, 2018

(54) ANTIOXIDANT AND ANTIMICROBIAL WOUND DRESSING MATERIALS

(71) Applicant: KCI USA, Inc., San Antonio, TX (US)

(72) Inventors: Deborah Addison, Keasden (GB); David Greenhalgh, Skipton (GB); Breda Mary Cullen, Skipton (GB)

(73) Assignee: KCI USA, Inc., San Antonio, TX (US)

( * ) Notice: Subject to any disclaimer, the term of this patent is extended or adjusted under 35 U.S.C. 154(b) by 0 days.

(21) Appl. No.: 14/598,016

(22) Filed: Jan. 15, 2015

(65) Prior Publication Data

US 2015/0352244 A1 Dec. 10, 2015

Related U.S. Application Data

(63) Continuation of application No. 13/406,470, filed on Feb. 27, 2012, now Pat. No. 8,962,908, which is a
(Continued)

(30) Foreign Application Priority Data

Nov. 18, 2003 (GB) .................................. 0326844.8

(51) Int. Cl.
*A61F 13/02* (2006.01)
*A61L 15/44* (2006.01)
(Continued)

(52) U.S. Cl.
CPC .......... *A61L 15/44* (2013.01); *A61F 13/0203* (2013.01); *A61F 13/0206* (2013.01);
(Continued)

(58) Field of Classification Search
CPC .......... A61L 15/28; A61L 15/64; A61L 15/44; A61L 15/46; A61L 15/325; A61L 15/56;
(Continued)

(56) References Cited

U.S. PATENT DOCUMENTS 2,296,856 A 9/1942 Lilienfeld
3,122,479 A 2/1964 Smith
(Continued)

FOREIGN PATENT DOCUMENTS

EP 0 368 253 A2 5/1990
EP 0437095 A2 7/1991
(Continued)

OTHER PUBLICATIONS

Kalirajan et al; Docking Studies, Synthesis, Characterization and Evaluation of their Antioxidant and Cytotoxic Activities of Some Novel Isoxazole-Substituted 9-Anilinoacridine Derivatives; The Scientific World Journal; vol. 2012, Article ID 165258.*
(Continued)

*Primary Examiner* — Ophelia A Hawthorne
*Assistant Examiner* — Caitlin Carreiro
(74) *Attorney, Agent, or Firm* — Foley & Lardner LLP

(57) ABSTRACT

A wound dressing material may include a polymeric substrate, a silver salt, and a dyestuff to photostabilize the silver salt. The substrate may include collagen and/or oxidized regenerated cellulose complexed to Ag+, and the dyestuff may, for example, be an aniline or acridine dye. Also disclosed are methods of making such materials, and wound dressings that include such materials.

41 Claims, 3 Drawing Sheets

Figure 1:
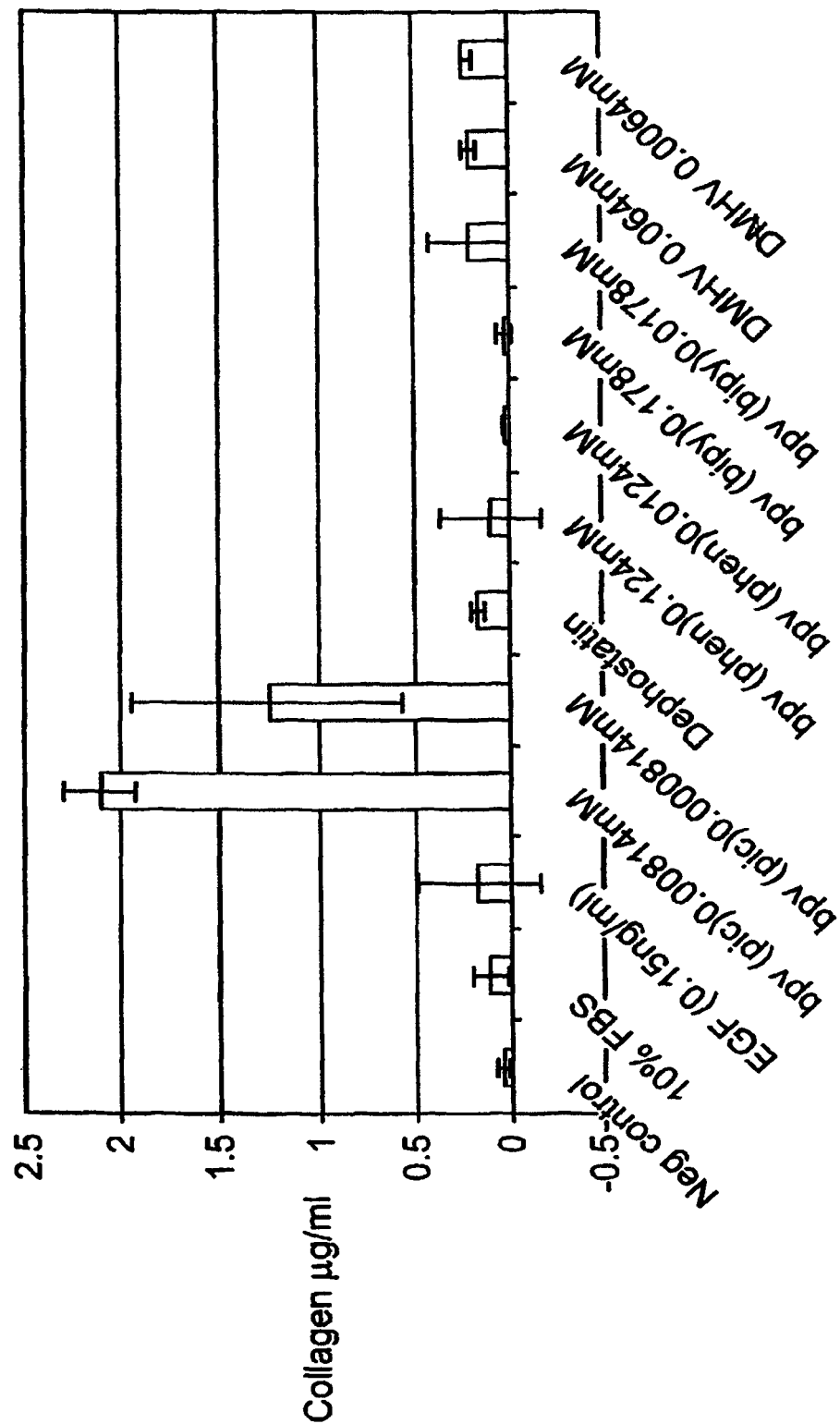
Figure 2:
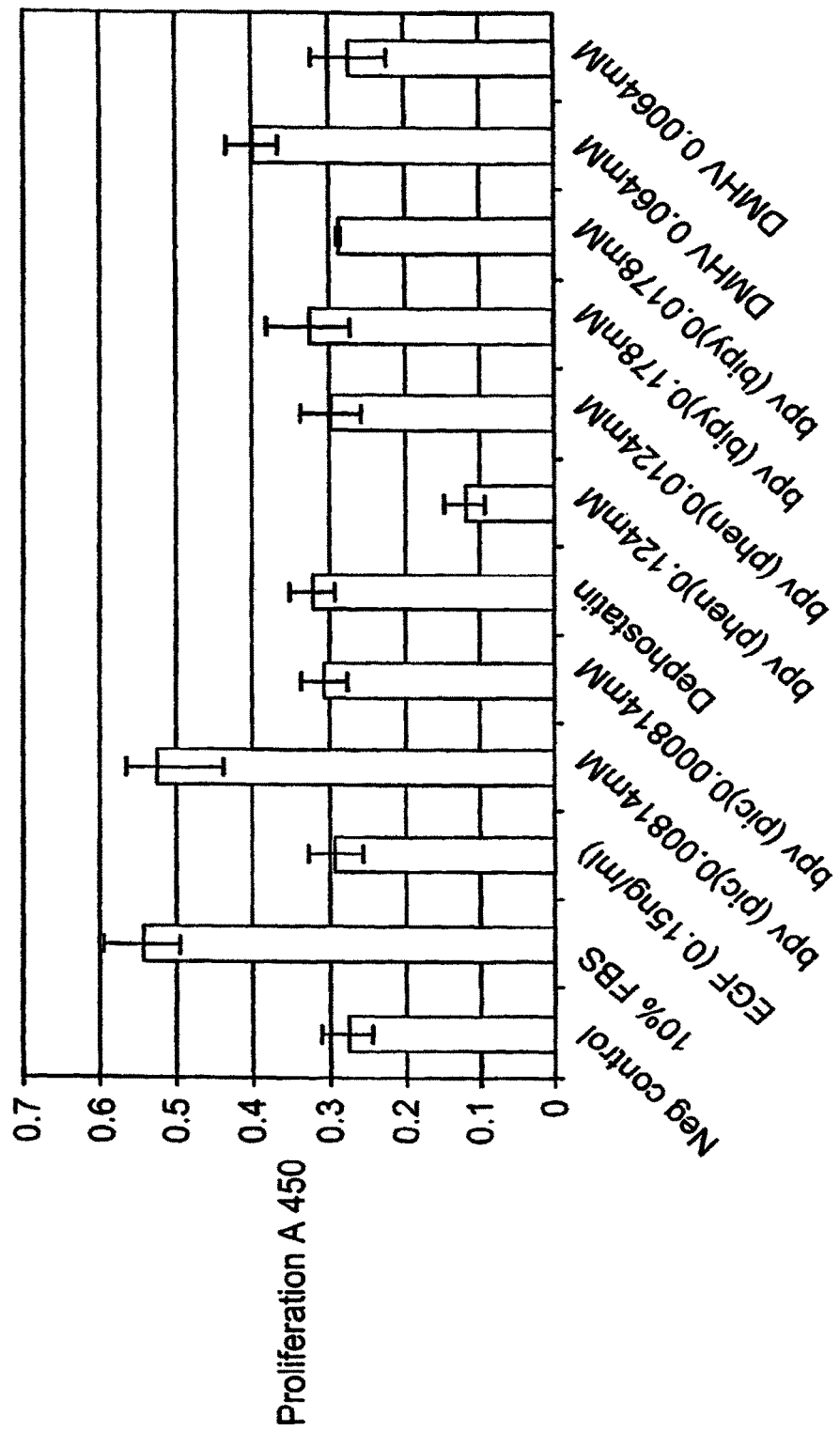
Figure 3:
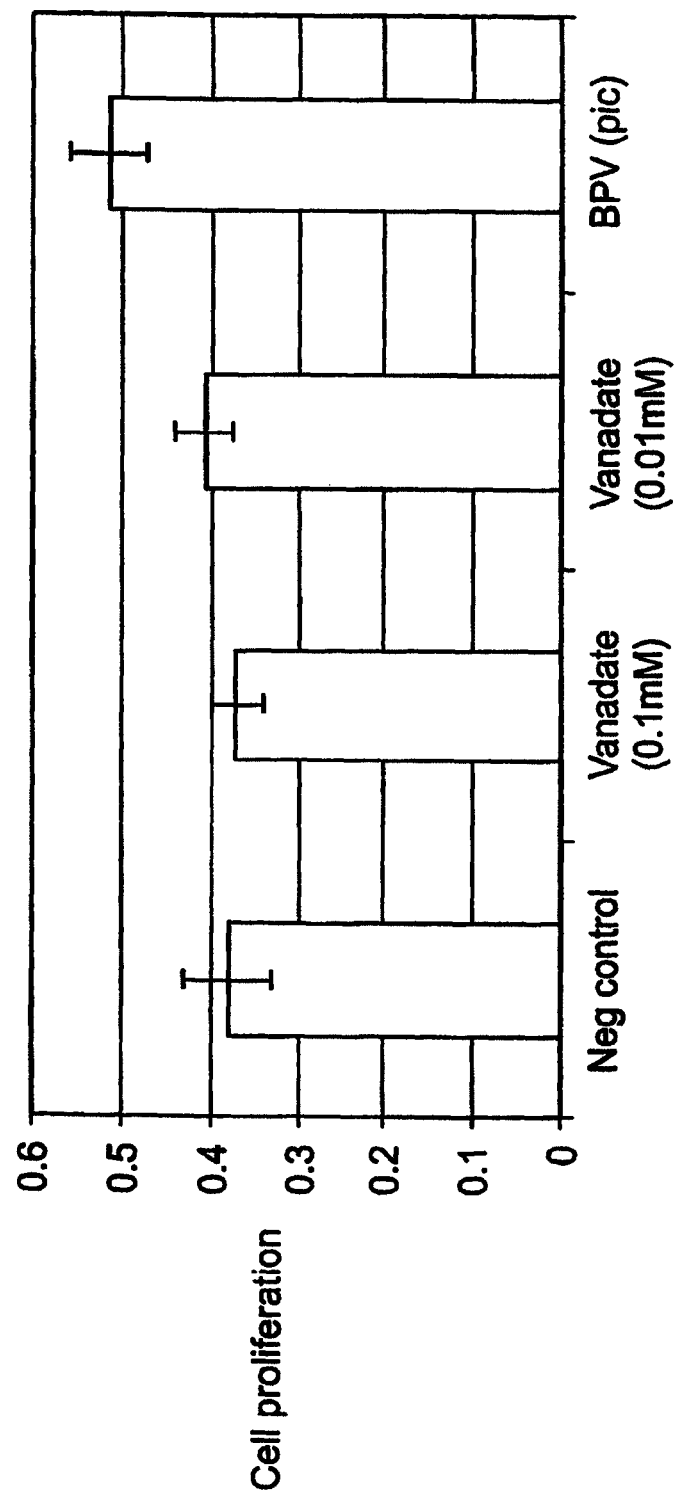

Related U.S. Application Data continuation of application No. 10/579,850, filed as application No. PCT/GB2004/004838 on Nov. 17, 2004, now Pat. No. 8,124,826.

(51) Int. Cl.

| | | |
|---|---|---|
| *B65B 5/04* | (2006.01) | |
| *B65B 55/12* | (2006.01) | |
| *A61L 15/20* | (2006.01) | |
| *A61L 15/28* | (2006.01) | |
| *A61L 15/32* | (2006.01) | |
| *A61L 15/46* | (2006.01) | |
| *A61L 15/56* | (2006.01) | |
| *A61L 15/64* | (2006.01) | |

(52) U.S. Cl.
CPC ...... *A61F 13/0209* (2013.01); *A61F 13/0213* (2013.01); *A61F 13/0226* (2013.01); *A61F 13/0256* (2013.01); *A61L 15/20* (2013.01); *A61L 15/28* (2013.01); *A61L 15/325* (2013.01); *A61L 15/46* (2013.01); *A61L 15/56* (2013.01); *A61L 15/64* (2013.01); *B65B 5/04* (2013.01); *B65B 55/12* (2013.01); *A61L 2300/21* (2013.01); *A61L 2300/404* (2013.01)

(58) Field of Classification Search
CPC ......... A61L 2300/404; A61L 2300/412; A61L 15/20; A61L 2300/21; A61L 2300/104; A61L 2300/204; A61L 15/32; C08L 1/24; C08L 5/08; C08L 1/00; C08L 23/22; C08L 1/04; C08L 35/04; C08L 53/02; C08L 5/00; C08L 5/04; C08L 83/04; A61F 13/0213; A61F 13/0209; A61F 13/0226; A61F 13/069; A61F 13/02
USPC .................................................... 602/42–54
See application file for complete search history.

(56) References Cited

U.S. PATENT DOCUMENTS

| | | | |
|---|---|---|---|
| 4,291,013 A | | 9/1981 | Wahlig et al. |
| 4,793,337 A | * | 12/1988 | Freeman ............. A61F 13/0253 428/370 |
| 5,326,567 A | | 7/1994 | Capelli |
| 5,338,565 A | * | 8/1994 | Shlenker ................ A01N 25/10 128/844 |
| 5,612,321 A | | 3/1997 | Nguyen |
| 5,667,501 A | | 9/1997 | Fowler et al. |
| 5,681,579 A | * | 10/1997 | Freeman ............. A61F 13/0203 424/447 |
| 6,136,835 A | | 10/2000 | Camden |
| 6,255,858 B1 | | 7/2001 | Akiyama et al. |
| 6,333,093 B1 | | 12/2001 | Burrell et al. |
| 6,361,786 B1 | | 3/2002 | Shanbrom |
| 6,468,521 B1 | | 10/2002 | Pedersen et al. |
| 6,605,667 B1 | * | 8/2003 | Badejo ................. A61L 24/001 424/443 |
| 6,897,349 B2 | | 5/2005 | Gibbins et al. |
| 7,118,761 B2 | | 10/2006 | Canada et al. |
| 7,732,655 B2 | | 6/2010 | Cullen et al. |
| 8,124,826 B2 | | 2/2012 | Addison et al. |
| 8,461,410 B2 | | 6/2013 | Cullen et al. |
| 8,962,908 B2 | | 2/2015 | Addison et al. |
| 2003/0007957 A1 | | 1/2003 | Britton et al. |
| 2003/0186955 A1 | | 10/2003 | Vange et al. |
| 2004/0101548 A1 | | 5/2004 | Pendharkar |
| 2005/0037680 A1 | | 2/2005 | Canada et al. |
| 2005/0113510 A1 | | 5/2005 | Feldstein et al. |
| 2005/0123590 A1 | * | 6/2005 | Burton ................. A61L 15/225 424/445 |
| 2006/0141015 A1 | | 6/2006 | Tessier et al. |
| 2007/0003603 A1 | | 1/2007 | Karandikar et al. |
| 2007/0166438 A1 | | 7/2007 | Kitahata et al. |
| 2008/0003906 A1 | | 1/2008 | Hill et al. |

FOREIGN PATENT DOCUMENTS

| | | | | |
|---|---|---|---|---|
| EP | 0541391 A1 | | 5/1993 | |
| EP | 0838491 B1 | | 4/2002 | |
| EP | 1153622 B1 | | 10/2004 | |
| GB | 684513 A | | 12/1952 | |
| GB | 1280631 A | | 7/1972 | |
| WO | WO-87/05517 A1 | | 9/1987 | |
| WO | WO 8705517 A1 | * | 9/1987 | ............. A01N 43/16 |
| WO | 91/11206 A1 | | 8/1991 | |
| WO | 9702038 A1 | | 1/1997 | |
| WO | 9800180 A1 | | 1/1998 | |
| WO | 9800446 A1 | | 1/1998 | |
| WO | 0124839 A1 | | 4/2001 | |
| WO | 0243743 A1 | | 6/2002 | |
| WO | 04026200 A2 | | 4/2004 | |
| WO | 04/112850 A1 | | 12/2004 | |

OTHER PUBLICATIONS

Blois, M.S. Nature 181:1199 (1958).
Banda, P.W. et al., Analytical Letters 7:41 (1974).
Cullen et al., "The role of oxidised regenerated cellulose/collagen in chronic wound repair and its potential mechanism of action," Intl J Biochem Cell Bio, 34(12):1544-56 (2002). (Abstract Only).
Non-Final Office Action in U.S. Appl. No. 14/980,681, dated Oct. 13, 2017 (21 pages).

* cited by examiner

ANTIOXIDANT AND ANTIMICROBIAL WOUND DRESSING MATERIALS

CROSS-REFERENCE TO RELATED APPLICATIONS

This application is a continuation of U.S. patent application Ser. No. 13/406,470, filed Feb. 27, 2012, now U.S. Pat. No. 8,962,908, which is a continuation of U.S. patent application Ser. No. 10/579,850, filed May 17, 2006, now U.S. Pat. No. 8,124,826, which is a National Stage Application under 35 U.S.C. 371 of PCT/GB2004/004838, filed Nov. 17, 2004, which claims priority from GB0326844.8 filed Nov. 18, 2003. The subject matter of this application is related to the subject matter of U.S. Ser. No. 10/305,040, filed Nov. 26, 2002. The content of each aforementioned application is expressly incorporated herein by reference thereto.

FIELD

The present invention relates to antimicrobial wound dressing materials, to processes suitable for the preparation of such materials, and to the use of such materials in the manufacture of wound dressings.

DISCUSSION

The antimicrobial effect of silver has been known for centuries. However, the precise mode of action of silver salts in killing microbes is yet to be established. It is known that silver salts bind with particular avidity to DNA and RNA. Silver salts also bind with particular strength to a variety of organic molecules such as: carboxylic acids, thiols, phenols, amines, phosphates and halogenated compounds. Following binding to proteins, those with enzymic activity are usually deactivated. The oxidative-reductive powers of silver and silver salts must also be reckoned with.

It is known to use metallic silver as an antimicrobial, whether in the form of thin films, nanoparticles or colloidal silver. Chemical compounds of silver are also useful as antimicrobials. For example, the following complex silver salts are favoured for use against sensitive and resistant bacterial strains:

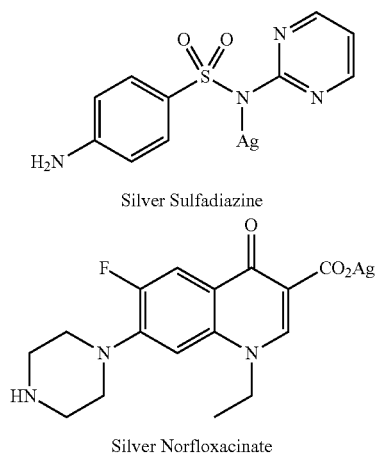

Silver Sulfadiazine

Silver Norfloxacinate

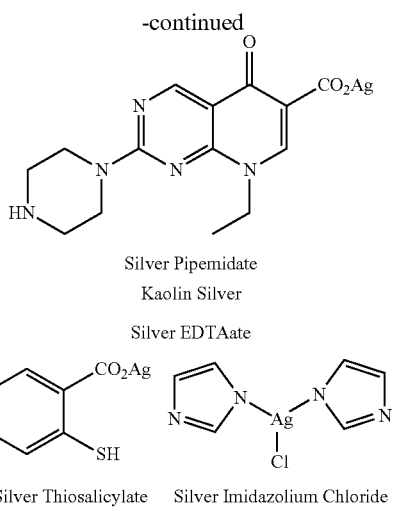

Silver Pipemidate

Kaolin Silver

Silver EDTAate

Silver Thiosalicylate   Silver Imidazolium Chloride

WO91/11206 describes the use of silver alginate salts in wound dressings. WO87/05517 describes silver salts of hyaluronic acid that may be used as or in antimicrobial wound dressings. These materials tend not to be stable in the presence of light. The silver undergoes photochemical reduction to metallic silver, causing a darkening of the materials over time.

WO02/43743 describes light-stabilized antimicrobial wound dressing materials in which silver salts are stabilized by the addition of a photostabilizer selected from the group consisting of ammonium salts, thiosulfates, metal chlorides and peroxides. Such photostabilizers are of limited effectiveness, and will tend to be extracted from the dressing material by wound fluid.

A need therefore remains for improved antimicrobial dressings containing light-stabilized silver compounds.

Concentrations of reactive oxygen species such as hydroxyl radicals (.OH), singlet oxygen ($^1O_2$), hydroperoxyl radicals (.OOH), superoxideradical anions (.$O_2$), and hydrogen peroxide ($H_2O_2$) can rise in damaged tissues, producing a condition known as oxidative stress. The presence of a low level of reactive oxygen species may be advantageous in the early stages of wound healing by both attracting and activating macrophages which engulf and kill bacteria and release cytokines and growth factors. Under mild oxidative stress conditions when hydrogen peroxide levels are slightly raised (around $10^{-8}$ to $10^{-4}$ molar), it has also been found that the rate of cell proliferation in fibroblast cultures is stimulated. However, prolonged and more severe oxidative stress may delay healing because it will produce chronic inflammation, divert available energy supply towards antioxidant defense at the expense of tissue reconstruction, and increase levels of matrix metalloproteinases which cause tissue breakdown. In more severe cases, elevated levels of reactive oxygen species can give rise to hydrogen peroxide-induced senescence or apoptosis (that is, programmed cell death) or tissue necrosis (that is, uncontrolled cell death and therefore permanent tissue damage).

Accordingly, the healing of chronic wounds may be assisted by the use of antioxidant wound dressings that react specifically with excess reactive oxygen species such as those listed above and hence reduce the level of oxidative stress.

U.S. Pat. No. 5,667,501 describes compositions comprising chemically modified polymers grafted with chemical groups that confer antioxidant activity as measured by a diphenylpicrylhydrazyl (DPPH) test and that also generate low levels of hydrogen peroxide by reaction with molecular oxygen in the wound bed to stimulate macrophage activity and fibroblast proliferation. The compositions may be used to promote the healing of chronic wounds. Preferably, the polymer is a polymer bearing hydroxyl, carbonyl or amide functional groups, or a polysaccharide bearing hydroxyl functional groups, said functional groups having been converted to derivatives that are persistent free radicals or precursors of persistent free radicals, that is to say they are free-radical-scavenging antioxidant groups.

U.S. Pat. No. 5,612,321 describes compositions comprising polysaccharides grafted with antioxidants on at least one hydroxyl group of the polysaccharide. The compositions may be used inter alia to promote the healing of chronic wounds. Preferably, the polysaccharide is hyaluronic acid and the antioxidant group comprises a phenol group.

The above antioxidant wound dressing materials are made by multi-step chemical reactions to achieve covalent bonding of antioxidant moieties, such as hydroquinones or benzimidazole derivatives, to the polymeric substrate materials.

A need therefore remains for a more simple and inexpensive route to antioxidant wound dressing materials.

DESCRIPTION

In a first aspect, the present invention provides a wound dressing material comprising a polymeric substrate, a silver salt, and a dyestuff to photostabilize the silver salt.

The wound dressing materials according to the present invention may be provided in the form of gels, beads, flakes, powder, and preferably in the form of a film, a fibrous pad, a web, a woven or non-woven fabric, a freeze-dried sponge, a foam or combinations thereof. In certain embodiments, the material is selected from the group consisting of woven fabrics, knitted fabrics, and nonwoven fabrics, all of which may be made by conventional methods. In other embodiments, the material may comprise (or consist essentially of) a freeze-dried sponge or a solvent-dried sponge. Methods of making freeze-dried and solvent-dried sponges are described in EP-A-1153622 and EP-A-0838491, the entire contents of which are incorporated herein by reference.

The wound dressing material is typically in sheet form, for example having an area of from about 1 cm$^2$ to about 400 cm$^2$, in particular from about 2 cm$^2$ to about 100 cm$^2$. The basis weight of the sheet is typically from about 100 g/m$^2$ to about 5000 g/m$^2$, for example from about 400 g/m$^2$ to about 2000 g/m$^2$.

The polymeric substrate may make up at least 50% by weight of the wound dressing material, for example at least 75% by weight or at least 90% by weight. The substrate polymer is usually not water soluble, but it may be water swellable.

The polymeric substrate may be bioabsorbable or non-bioabsorbable. The term "bioabsorbable polymer" refers to a polymer that is fully degraded and absorbed in vivo in the mammalian body.

Suitable non-bioabsorbable polymers include common textile materials such as cellulose, processed cellulose such as viscose, polyamide, polyurethane, and also alginates.

Suitable bioabsorbable polymers include those selected from the group consisting of collagens, bioabsorbable cellulose derivatives such as oxidized celluloses, galactomannans such as guar/borate, glycosaminoglycans such as cross-linked hyaluronates, polylactides/polyglycolides, polyhydroxybutyrates, and mixtures thereof.

In certain preferred embodiments the polymeric substrate comprises (and may consist essentially of) a solid bioabsorbable material selected from the group consisting of collagens, chitosans, oxidized celluloses, and mixtures thereof.

Oxidized cellulose is produced by the oxidation of cellulose, for example with dinitrogen tetroxide. This process converts primary alcohol groups on the saccharide residues to carboxylic acid group, forming uronic acid residues within the cellulose chain. The oxidation does not proceed with complete selectivity, and as a result hydroxyl groups on carbons 2 and 3 are occasionally converted to the keto form. These ketone units introduce an alkali labile link, which at pH7 or higher initiates the decomposition of the polymer via formation of a lactone and sugar ring cleavage. As a result, oxidized cellulose is biodegradable and bioabsorbable under physiological conditions.

The preferred oxidized cellulose for practical applications is oxidized regenerated cellulose (ORC) prepared by oxidation of a regenerated cellulose, such as rayon. It has been known for some time that ORC has haemostatic properties, and that application of ORC fabric can be used to reduce the extent of post-surgical adhesions in abdominal surgery.

The oxidized regenerated cellulose (ORC) can be obtained by the process described in U.S. Pat. No. 3,122,479, the entire content of which is incorporated herein by reference. This material offers numerous advantages including the features that it is biocompatible, biodegradable, non-immunogenic and readily commercially available. ORC is available with varying degrees of oxidation and hence rates of degradation. The ORC may be used in the form of insoluble fibers, including woven, non-woven and knitted fabrics. In other embodiments, the ORC is in the form of water-soluble low molecular weight fragments obtained by alkali hydrolysis of ORC.

In certain embodiments, the oxidized cellulose is in the form of particles, such as fiber particles or powder particles, for example dispersed in a suitable solid or semisolid topical medicament vehicle. In particular, the materials preferably contain ORC fibers, wherein a volume fraction of at least 80% of the fibers have lengths in the range of 20 μm to 1000 μm. Such a size distribution can be achieved, for example, by milling an ORC cloth, followed by sieving the milled powder to remove fibers outside the range. Preferably, the average (mean by volume) length of the ORC fibers is in the range 250 μm to 450 μm. The selection of ORC fiber lengths in this range results in easy mixing of the ORC and other components and highly homogeneous products.

Preferably, the oxidised cellulose has an average molecular weight greater than 50,000. Such oxidised cellulose is substantially insoluble in wound fluids, but will undergo very gradual breakdown into bioresorbable fragments at physiological pH. Preferably, the oxidized cellulose is not neutralized. However, the present invention encompasses the use of partially or completely neutralised materials as described in EP-A-0437095. Especially suitable materials are made if the neutralization is carried out partially or completely with the silver salt of a weak acid, such as silver acetate.

Chitin is a natural biopolymer composed of N-acetyl-D-glucosamine units. Chitin may be extracted from the outer shell of shrimps and crabs in known fashion. The chitin is then partially deacetylated, for example by treatment with 5M-15M NaOH, to produce chitosan. Complete deacetylation of the chitin is not a practical possibility, but preferably the chitosan is at least 50% deacetylated, more preferably at least 75% deacetylated. Chitosan has been employed for wound treatment in various physical forms, e.g. as a solution/gel; film/membrane; sponge; powder or fiber. Chitosan in the free base form is swellable but not substantially soluble in water at near-neutral pH, but soluble in acids due to the presence of ammonium groups on the chitosan chain. The solubility of the chitosan may be reduced by cross-linking, for example with epichlorhydrin. Typically, the average molecular weight of the chitosan as determined by gel permeation chromatography is from about 105 to about 106.

The collagen useful as the polymeric substrate on the materials according to the present invention may be any collagen, including Type I or Type II or Type III collagen, natural fibrous collagen, atelocollagen, partially hydrolysed collagens such as gelatin, and combinations thereof. Natural fibrous collagen, for example of bovine origin, is suitable. For example, the collagen prepared from bovine hide is a combination of Type I collagen (85%) and Type III collagen (15%).

In certain embodiments of the present invention, the oxidized cellulose is complexed with collagen and/or chitosan to form structures of the kind described in WO98/00180, WO98/00446 or WO2004/026200, the entire contents of which are expressly incorporated herein by reference. For example, the oxidized cellulose may be in the form of milled ORC fibres that are dispersed in a freeze-dried collagen or chitosan sponge. This provides for certain therapeutic and synergistic effects arising from the complexation with collagen.

In particular embodiments, the polymeric substrate comprises (and may consist essentially of) a mixture of: (a) collagen and/or chitosan; and (b) oxidized regenerated cellulose, for example in a dry weight ratio range of from about 90:10 to about 10:90 of collagen/chitosan:ORC, preferably from about 75:25 to about 25:75, and particularly from about 60:40 to about 40:60.

Preferably, the amount of silver (as silver ions and metallic silver) in the materials according to the present invention is from about 0.01 wt % to about 5 wt. %, more preferably from about 0.1 wt % to about 2 wt. %, and most preferably about 0.1 wt. % to about 1 wt. %, most preferably about 0.3 wt. %. Lesser amounts of silver could give insufficient antimicrobial effect. Greater amounts of silver could give rise to antiproliferative effects on wound healing cells.

The silver may be introduced by treating the polymeric substrate material with a silver salt or compound dissolved or dispersed in water or an organic solvent such as ethanol, for example as described in WO02/43743. Suitable compounds include silver oxide, silver chromate, silver allantoinate, silver borate, silver glycerolate, silver nitrate, silver acetate, silver chloride, silver sulfate, silver lactate, silver bromide, silver iodide, silver carbonate, silver citrate, silver laurate, silver deoxycholate, silver salicylate, silver p-aminobenzoate, silver p-aminosalicylate, and mixtures thereof. Preferably, the silver is not present as silver sulfadiazine.

In preferred embodiments, the silver may be complexed to the polymeric substrate material. The term "complex" refers to an intimate mixture at the molecular scale, preferably with ionic or covalent bonding between the silver and the polymer. The complex preferably comprises a salt formed between an anionic polymer and Ag+. Suitably, the anionic polymer is a polycarboxylate. Suitably, the anionic polymer comprises an anionic polysaccharide or a polyacrylate. Suitable anionic polysaccharides include alginates, hyaluronates, pectins, carrageenans, xanthan gums, sulfated polysaccharides such as dermatan sulfate or sulfated dextrans, and carboxylated cellulose derivatives such as carboxymethyl celluloses and oxidized celluloses.

The complex of an anionic polymer and silver can be made by a method comprising the step of treating an anionic polymer with a solution of a silver salt. Preferably, the solution is an aqueous solution. Preferably, the anionic polymer is substantially insoluble in water at pH7, and the treatment is therefore carried out on the polymer in the solid state. For example, the polymer may be in the form of solid fibers, sheet, sponge or fabric. In certain embodiments, the anionic polymer is a salt and the treatment therefore can be regarded as an ion exchange. In other embodiments, the anionic polymer is at least partly in free acid form, in which case the silver salt is preferably a salt of a weak acid, for example silver acetate, whereby the anionic polymer is at least partially neutralised by the silver salt. Similar processes are described in EP-A-0437095, the entire content of which is expressly incorporated herein by reference.

The neutralization reaction can be carried out in water or alcohol alone but is preferably carried out in mixtures of water and alcohols. The use of a mixture of water and alcohol provides good solubility for the weak acid salts via the water, and the alcohol prevents the anionic polymer from excessively swelling, distorting and weakening during the neutralization. Thus the physical properties of the material are retained. Methanol is the preferred alcohol because many of the above-mentioned salts have good solubility in this alcohol in combination with water. Preferably, the alcohol to water ratio has a range of about 4:1 to 1:4. If the solution becomes too rich in alcohol, some salts may no longer be soluble particularly if the alcohol is other than methanol. If the solution becomes too rich in water, some swelling of the polymer will occur as neutralization takes place and there will be some loss in physical properties such as in the tensile strength of the polymer. Other useful alcohols include, for example, ethyl alcohol, propyl alcohol and isopropyl alcohol.

The use of a mild neutralizing agent such as silver acetate allows for control of the degree of neutralization. Use of stoichiometric and chemically equivalent amounts of neutralizing agent and carboxylic acid on the anionic polymer does not produce a 100% neutralized polymer as would be produced with strong irreversible reactions with bases such as sodium hydroxide, sodium carbonate, sodium bicarbonate and ammonium hydroxide.

Anionic polymers behave as an ion exchanger and will pull out of solution the silver cation of any silver salt that is passed over them. The by-product of this exchange is an acid from the salt and by using a salt of a weak organic acid, a weak acid such as acetic acid is produced which does no damage to the polymer. Using salts of strong acids such as sodium chloride or sodium sulfate produces hydrochloric acid or sulfuric acid by-products respectively, and these strong acids can cause damage such as depolymerization of the polymer.

When using silver salts of weak acids, the silver ion is exchanged for a proton on the polymer and part of the salt is converted to weak acid. The mixture of acid and salt in the solution results in a buffered solution which maintains a fairly constant pH and controls the degree of neutralization. An equilibrium reaction is established whereby the silver ions are bound to the acid portion of the polymer and also to the salt molecules. This partitioning of the silver ions prevents the neutralization of the polymer from going to completion.

Using a stoichiometric amount of, for example, silver acetate brings about a 65-75% degree of neutralization of the carboxylic acid groups on an oxidized cellulose polymer. This control of pH by creating a self generating buffered solution and the use of methanol to control the swelling of the material, leads to a partially neutralized material in which the physical properties, e.g. tensile strength and shape of the polysaccharide, are preserved.

The amount of silver salt used is generally about equal to or up to twice the stoichiometric amount of carboxylic acid content of the polysaccharide. Alternatively, a second charge of a stoichiometric amount of silver salt can be used if the reaction is recharged with fresh solvent and salt after the first charge reaches a constant pH. The material with elevated pH is then washed to remove the excess silver salt and ions therefrom.

In certain embodiments, at least a portion of the wound dressing material comprises a collagen complexed with silver. This can be achieved by treating a collagen with a solution of a silver salt. The silver salt may for example be silver acetate or silver nitrate at a concentration of about 0.01 molar to about 1 molar. The treatment is preferably carried out at a pH of from about 5 to about 9. It is thought that the silver complexes primarily to the nitrogen-containing side chains of the collagen amino acids, in particular to lysine, hydroxylysine, asparagine, glutamine and arginine. The silver could also bind to the sulfhydryl groups of methionine and cysteine residues, where present, and to carboxyl groups of aspartate and glutamate.

Preferably the amount of silver in the collagen complex is from about 0.01 to about 30% by weight based on the weight of the collagen, more preferably from about 0.1% to about 20%, more preferably from about 2% to about 10% by weight. Preferably, the amount of silver-collagen complex in the wound dressing material is from about 0.1 to about 10 wt. %, more preferably from about 0.1 to about 2 wt. %. In any case, the total amount of silver in the wound dressing material is generally as specified above.

It will be appreciated that the complexes of silver with polysaccharides described above may be prepared with a relatively high silver content, for example greater than 5 wt. %, and then diluted with further polysaccharide (the same or different) to achieve the desired overall silver content of from 0.01 wt. % to 5 wt. %, preferably from about 0.2 wt. % to about 2 wt. %.

The term "dyestuff" refers to a material that is useful as a colorant for textile materials, that is to say an organic compound that is strongly light-absorbing in the visible region 400-700 nm and that binds in substantially water-tight fashion to textile materials such as cellulose fabrics. The dyestuffs can stabilize the silver salts against photochemical decomposition by absorbing light near the surface of the material. The dyestuffs also trap photochemically generated free radicals that could otherwise react with the silver. In this way the dyestuffs can act as photochemical desensitisers.

The dyestuffs may be any suitable, medically acceptable dyestuff that stabilizes silver salts against photochemical reduction to metallic silver. Medically acceptable organic desensitisers of the kind used in photography are suitable. Also suitable are the so-called antioxidant dyestuffs.

In certain embodiments, the antioxidant dyestuff is selected from the group consisting of aniline dyes, acridine dyes, thionine dyes, bis-naphthalene dyes, thiazine dyes, azo dyes, anthraquinone dyes, and mixtures thereof. For example, the antioxidant dyestuff may be selected from the group consisting of gentian violet, aniline blue, methylene blue, crystal violet acriflavine, 9-aminoacridine, acridine yellow, acridine orange, proflavin, quinacrine, brilliant green, trypan blue, trypan red, malachite green, azacrine, methyl violet, methyl orange, methyl yellow, ethyl violet, acid orange, acid yellow, acid blue, acid red, thioflavin, alphazurine, indigo blue, methylene green, and mixtures thereof.

The dyestuff may be present in the wound dressing material according to the invention in an amount of from about 0.05% to about 5 wt. %, typically about 0.2 to about 2 wt. % based on the dry weight of the material.

The step of dyeing may be carried out either before, concurrently with, or after the step of silver treatment, but preferably it is not carried out after the treatment with silver in order to avoid leaching of silver into the dye bath.

It has been found that medically acceptable polymeric substrate materials such as oxidized regenerated cellulose have excellent avidity for dyes, such as the antioxidant dyes listed above. This enables controlled amounts of the dyes to be fixed onto the substrate materials in a simple and inexpensive dyeing step. The dyes act as photochemical desensitizers to stabilize the silver salts against photochemical reduction. It has further been found that, when antioxidant dyes are used, the resulting dyed materials retain the antioxidant properties of the dyestuff, thereby making them excellent candidates for the treatment of chronic wounds and other wounds characterised by elevated levels of oxygen free radicals.

The wound dressing materials according to the present invention may also comprise up to 20% by weight, preferably less than 10% by weight of water. The material may also contain 0-40% by weight, preferably 0-25% by weight of a plasticiser, preferably a polyhydric alcohol such as glycerol. The material may also comprise 0-10% by weight, preferably 0-5% by weight of one or more additional therapeutic wound healing agents, such as non-steroidal anti-inflammatory drugs (e.g. acetaminophen), steroids, antibiotics (e.g. penicillins or streptomycins), antiseptics other than silver (e.g. chlorhexidine), or growth factors (e.g. fibroblast growth factor or platelet derived growth factor). All of the above percentages are on a dry weight basis.

The wound dressing material according to the present invention is preferably sterile and packaged in a microorganism-impermeable container.

Preferably, the material according to the present invention has a free radical activity, that is to say an antioxidant activity, of at least about 15% in the diphenylpicrylhydrazyl (DPPH) test, measured as percentage reduction in absorbance at 524 nm after 4 hours of a 0.5% w/v dispersion of the polysaccharide in $10^{-4}$M DPPH, as described further hereinbelow in Procedure 1. Preferably the percentage reduction in absorbance in the DPPH test (after correction for any absorbance by the dye) is at least about 25%, more preferably at least about 50%, and most preferably at least about 75%.

Alternatively or additionally, the material according to the present invention may exhibit antioxidant activity as measured by its ability to inhibit the oxidation of ABTS (2,2'-azino-di-[3-ethylbenzthiazoline sulphonate]) by a peroxidase.

Preferably, the materials according to the present invention exhibit antimicrobial ability against at least *Staphylococcus aureus* and *Pseudomonas aeruginosa*, and preferably also against *Salmonella choleraesuis* and *Candida albicans*, as determined by the zone of clearance test described hereunder as Procedure 2.

Preferably, the material according to the present invention will absorb water or wound fluid and hence become wet, swell or become a gelatinous mass but will not spontaneously dissolve or disperse therein. That is to say, it is hydrophilic but has a solubility of preferably less than about 1 g/liter in water at 25° C. Low solubility renders such materials especially suitable for use as wound dressings to remove reactive oxygen species from the wound fluid.

The antioxidant and antimicrobial properties of the materials according to the present invention suggest applications in a range of medical applications, including the treatment of acute surgical and traumatic wounds, burns, fistulas, venous ulcers, arterial ulcers, pressure sores (otherwise known as decubitus ulcers), diabetic ulcers, ulcers of mixed aetiology, and other chronic or necrotic wounds and inflammatory lesions and disorders. The materials according to the present invention are primarily intended for the treatment of both infected wounds and non-infected wounds (that is to say wounds showing no clinical signs of infection).

Accordingly, in a further aspect the present invention provides the use of a material according to the present invention for the preparation of a medicament for the treatment of a wound. Preferably, the wound is a chronic wound and/or an infected wound. More preferably, the chronic wound is selected from the group consisting of ulcers of venous, arterial or mixed aetiology, decubitus ulcers, or diabetic ulcers.

In a related aspect, the present invention provides a method of treatment of a wound in a mammal comprising applying thereto a therapeutically effective amount of a material according to the present invention. Preferably, the wound is a chronic wound.

In a further aspect, the present invention provides a wound dressing comprising a wound dressing material according to the present invention.

The wound dressing is preferably in sheet form and comprises an active layer of the material according to the invention. The active layer would normally be the wound contacting layer in use, but in some embodiments it could be separated from the wound by a liquid-permeable top sheet. Preferably, the area of the active layer is from about 1 cm$^2$ to about 400 cm$^2$, more preferably from about 4 cm$^2$ to about 100 cm$^2$.

Preferably, the wound dressing further comprises a backing sheet extending over the active layer opposite to the wound facing side of the active layer. Preferably, the backing sheet is larger than the active layer such that a marginal region of width 1 mm to 50 mm, preferably 5 mm to 20 mm extends around the active layer to form a so-called island dressing. In such cases, the backing sheet is preferably coated with a pressure sensitive medical grade adhesive in at least its marginal region.

Preferably, the backing sheet is substantially liquid-impermeable. The backing sheet is preferably semipermeable. That is to say, the backing sheet is preferably permeable to water vapour, but not permeable to liquid water or wound exudate. Preferably, the backing sheet is also microorganism-impermeable. Suitable continuous conformable backing sheets will preferably have a moisture vapor transmission rate (MVTR) of the backing sheet alone of 300 to 5000 g/m$^2$/24 hrs, preferably 500 to 2000 g/m$^2$/24 hrs at 37.5° C. at 100% to 10% relative humidity difference. The backing sheet thickness is preferably in the range of 10 to 1000 micrometers, more preferably 100 to 500 micrometers. It has been found that such moisture vapor transmission rates allow the wound under the dressing to heal under moist conditions without causing the skin surrounding the wound to macerate.

Suitable polymers for forming the backing sheet include polyurethanes and poly alkoxyalkyl acrylates and methacrylates such as those disclosed in GB-A-1280631. Preferably, the backing sheet comprises a continuous layer of a high density blocked polyurethane foam that is predominantly closed-cell. A suitable backing sheet material is the polyurethane film available under the Registered Trade Mark ESTANE 5714F.

The adhesive (where present) layer should be moisture vapor transmitting and/or patterned to allow passage of water vapor therethrough. The adhesive layer is preferably a continuous moisture vapor transmitting, pressure-sensitive adhesive layer of the type conventionally used for island-type wound dressings, for example, a pressure sensitive adhesive based on acrylate ester copolymers, polyvinyl ethyl ether and polyurethane as described for example in GB-A-1280631. The basis weight of the adhesive layer is preferably 20 to 250 g/m$^2$, and more preferably 50 to 150 g/m$^2$. Polyurethane-based pressure sensitive adhesives are preferred.

Further layers of a multilayer absorbent article may be built up between the active layer and the protective sheet. For example, these layers may comprise an absorbent layer between the active layer and the protective sheet, especially if the dressing is for use on exuding wounds. The optional absorbent layer may be any of the layers conventionally used for absorbing wound fluids, serum or blood in the wound healing art, including gauzes, nonwoven fabrics, superabsorbents, hydrogels and mixtures thereof. Preferably, the absorbent layer comprises a layer of absorbent foam, such as an open celled hydrophilic polyurethane foam prepared in accordance with EP-A-0541391, the entire content of which is expressly incorporated herein by reference. In other embodiments, the absorbent layer may be a nonwoven fibrous web, for example a carded web of viscose staple fibers. The basis weight of the absorbent layer may be in the range of 50-500 g/m$^2$, such as 100-400 g/m$^2$. The uncompressed thickness of the absorbent layer may be in the range of from 0.5 mm to 10 mm, such as 1 mm to 4 mm. The free (uncompressed) liquid absorbency measured for physiological saline may be in the range of 5 to 30 g/g at 25°. Preferably, the absorbent layer or layers are substantially coextensive with the active layer.

The wound facing surface of the dressing is preferably protected by a removable cover sheet. The cover sheet is normally formed from flexible thermoplastic material. Suitable materials include polyesters and polyolefins. Preferably, the adhesive-facing surface of the cover sheet is a release surface. That is to say, a surface that is only weakly adherent to the active layer and the adhesive on the backing sheet to assist peeling of the adhesive layer from the cover sheet. For example, the cover sheet may be formed from a non-adherent plastic such as a fluoropolymer, or it may be provided with a release coating such as a silicone or fluoropolymer release coating.

Typically, the wound dressing according to the present invention is sterile and packaged in a microorganism-impermeable container.

In a further aspect, the present invention provides a method of manufacture of an antioxidant wound dressing material, comprising the steps of: dyeing a polymeric substrate material with a dye which stabilizes silver salts against photochemical reduction; and treating the substrate material with a silver salt dissolved or dispersed in water or an organic solvent.

The method according to the present invention may be used to prepare a wound dressing material according to the present invention.

The method of the present invention may comprise dyeing a substrate material in sheet form, for example a woven, nonwoven or knitted fabric or sponge sheet of the substrate material by immersing it in a dye bath, followed by washing to remove unbound dye, treatment with a silver salt as hereinbefore described, and drying. In other embodiments, the substrate material may be dyed while it is in fibrous or particulate form, followed by forming the material into a sheet. For example, a slurry of fibers or particles of the substrate material may be treated with dye, and then freeze-dried to form a dyed sponge. The silver treatment may be carried out on the slurry, or on the sponge after freeze-drying.

It will be appreciated that any feature or embodiment that is described herein in relation to any one aspect of the invention may also be applied to any other aspect of the invention.

Certain specific embodiments of the present invention will now be described further in the following examples

EXAMPLE 1

An antioxidant and antimicrobial wound dressing material based on a collagen/ORC freeze-dried sponge material is prepared as follows.

The collagen component is prepared from bovine corium as follows. Bovine corium is split from cow hide, scraped and soaked in sodium hypochlorite solution (0.03% w/v) to inhibit microbial activity pending further processing. The corium is then washed with water and treated with a solution containing sodium hydroxide (0.2% w/v) and hydrogen peroxide (0.02% w/v) to swell and sterilize the corium at ambient temperature. The corium splits then undergo an alkali treatment step in a solution containing sodium hydroxide, calcium hydroxide and sodium bicarbonate (0.4% w/v, 0.6% w/v and 0.05% w.v, respectively) at pH greater than 12.2, ambient temperature, and for a time of 10-14 days, with tumbling, until an amide nitrogen level less than 0.24 mmol/g is reached. The corium splits then undergo an acid treatment step with 1% hydrochloric acid at ambient temperature and pH 0.8-1.2. The treatment is continued with tumbling until the corium splits have absorbed sufficient acid to reach a pH less than 2.5. The splits are then washed with water until the pH value of corium splits reaches 3.0-3.4. The corium splits are then comminuted with ice in a bowl chopper first with a coarse comminution and then with a fine comminution setting. The resulting paste, which is made up in a ratio of 650 g of the corium splits to 100 g of water, as ice, is frozen and stored before use in the next stage of the process. However, the collagen is not freeze-dried before admixture with the ORC & other components in the next stage.

The ORC component of the freeze-dried pad is prepared as follows. A SURGICEL cloth (Johnson & Johnson Medical, Arlington) is milled using a rotary knife cutter through a screen-plate, maintaining the temperature below 60° C.

Methylene blue, an acidic dye, was incorporated by dissolving an appropriate amount of the dye in 0.05M acetic acid and adding to the collagen paste with the milled ORC powder to obtain a slurry. Samples were made in which tile dye was incorporated at the following concentrations in the final slurry: 0% (reference example), 1 mg/ml, 0.5 mg/ml and 0.1 mg/ml.

Silver is incorporated by dissolving silver acetate in 0.05M acetic acid and adding the solution to the slurry to achieve a final solids concentration in the slurry of about 1% w/w. The silver acetate is added in an amount sufficient to produce a final slurry containing 1 wt. % silver on a total solids basis.

The final slurry was poured into petri dishes to a depth of 3 mm, and placed onto freezer shelves where the temperature has been preset to −40° C. The freeze-drier programme was then initiated to dry and dehydrothermally cross-link the collagen and ORC to form sponge pads. On completion of the cycle, the vacuum was released, sponge samples were then packaged, and sterilized by cobalt 60 gamma-irradiation.

EXAMPLE 2

The procedure of Example 1 was followed, but replacing the methylene blue dye by crystal violet, a basic dye. The crystal violet was incorporated at the following concentrations in the slurry: 0% (reference example), 1 mg/ml, 0.5 mg/ml and 0.1 mg/ml.

EXAMPLE 3

The procedure of Example 1 was followed, but replacing the methylene blue dye by flavin 3,6-Diaminoacridine hemisulfate, a basic dye. The flavin was incorporated at the following concentrations in the slurry: 0% (reference example), 1 mg/ml, 0.5 mg/ml and 0.1 mg/ml.

EXAMPLE 4

The procedure of Example 1 was followed, but replacing the methylene blue dye by flavin 3,6-Diaminoacridine hemisulfate, a basic dye. The flavin was incorporated at the following concentrations in the slurry: 0% (reference example), 1 mg/ml, 0.5 mg/ml and 0.1 mg/ml.

EXAMPLE 5

The procedure of Example 1 was followed, but replacing the methylene blue dye by a mixture of methylene blue and flavin 3,6-Diaminoacridine hemisulfate, each dye being incorporated in the slurry at a concentration of 0.5 mg/ml.

EXAMPLE 6

The procedure of Example 1 was followed, but replacing the methylene blue dye by a mixture of crystal violet and flavin 3,6-Diaminoacridine hemisulfate, each dye being incorporated in the slurry at a concentration of 0.5 mg/ml.

EXAMPLE 7

The procedure of Example 1 was followed, but replacing the methylene blue dye by a mixture of crystal violet and methylene blue, each dye being incorporated in the slurry at a concentration of 0.5 mg/ml.

The sponges according to the invention obtained in Examples 1 to 7 all showed stable absorption of the dyes. The sponges could be been soaked in serum at 25° C. for a number of days and remained coloured at all times. Depending on concentration of dye added there was an initial release of the excess dye and then a gradual release as the sponges began to degrade.

Procedure 1

The ability of the wound dressing materials to react with and remove oxygen containing free radicals is assessed by the DPPH test described in WO94/13333, the entire content of which is expressly incorporated herein by reference. The test is adapted from that described by Blois M. S. in Nature 181: 1199 (1958), and Banda P. W. et al., in Analytical Letters 7:41 (1974).

Briefly, the wound dressing material under test (2.5 mg; 5 mg; & 25 mg sample sizes) was suspended in 2.5 ml of 0.1 M pH 7.0 phosphate buffer. A solution of diphenylpicrylhydrazyl (DPPH) in methanol (10-4 M) was added in an amount of 2.5 ml and the mixture was shaken and stored in the dark at 20° C. The samples were assessed by measurement of their light absorbance at 524 nm over 6 hours in comparison with a control, particular attention being paid to the figure after 4 hours. The percentage reduction of absorbance relative to the control after 4 hours gives the DPPH test value, with a reproducibility generally of ±5%. This value may conveniently be expressed in terms of a simple reduction in absorbance units (AU) relative to the control.

Ascorbic acid, a well-known antioxidant, provides a useful positive control substance for comparative purposes. Freeze-dried sponges of chitin/chitosan and hydroxyethyl cellulose were used as negative controls.

Application of this test resulted in DPPH test values of 80-90% for the positive control ($10^{-4}$M). In contrast, the negative controls chitin/chitosan and hydroxyethyl cellulose exhibited much lower DPPH values of less than 15%. The collagen/ORC without any added dye or silver exhibited some activity in the DPPH test, indicating that ORC itself has some antioxidant properties. The materials according to the present invention are expected to exhibit significantly higher activity in the DPPH test than collagen/ORC alone, consistent with antioxidant activity of the dyes.

Procedure 2

The bactericidal activity of the sponges prepared in Examples 1 to 7 is tested on *pseudomonas Aeruginosa* and *staphylococcus Aureus* by looking at zone of inhibition.

Six 2 cm×2 cm squares of each sample are cut out in sterile conditions. On day one of the experiment, cultures of both *Pseudomonas aeruginosa* (ATCC 27853 and various PSI strains) and *Staphylococcus aureus* (provided by the Dept of Clinical Microbiology and Pathology) are incubated aerobically at 37° C. for 24 hours on Diagnostic Sensitivity Agar (DSA). After 24 hours test samples are each placed on a DSA plate and immediately wetted with 0.5 mls of a buffer solution. Three squares of sample are placed on plates inoculated with *Pseudomonas aeruginosa* and three are placed on plates inoculated with *Staphylococcus aureus*. The plates are then incubated at 37° C. for 24 hours. The zone of inhibited growth around the sample is then measured using calipers, and the test sample is placed on a new inoculated DSA plate. A swab test is carried out on the area beneath the sample to determine if the sample is bacteriostatic if not bactericidal by smearing the swab on a DSA plate and incubating it for 24 hours and then examining the growth. The samples are transferred onto fresh inoculated plates with the above procedure being carried out every 24 hours for 72 hours as long as the samples remain intact.

As a negative control, a freeze dried sponge of 45% ORC/55% collagen without any silver or dye was tested. A commercially available silver-containing antimicrobial dressing (ACTICOAT, registered trade mark of Smith & Nephew) and silver nitrate solution (0.5%) were used as positive controls and zones of inhibition were observed for both over the test period.

It is found that significant bactericidal effects are observed against *Staphylococcus aureus* and *Pseudomonas Aeruginosa* for the materials according to the invention.

The performance of the materials containing 1% silver and above is expected to be comparable to that of the ACTICOAT dressing.

The above embodiments have been described by way of example only. Many other embodiments falling within the scope of the accompanying claims will be apparent to the skilled reader.

The invention claimed is:

1. A method of manufacture of an antioxidant wound dressing material, comprising the steps of: dyeing a polymeric substrate material with a dye which stabilizes silver salts against photochemical reduction; and treating the substrate material with a silver salt dissolved or dispersed in water or an organic solvent.

2. The method according to claim 1, wherein the polymeric substrate material comprises a solid bioabsorbable material.

3. The method according to claim 2, wherein the solid bioabsorbable material comprises collagens, oxidized celluloses, chitosans, galactomannans, or glycosaminoglycans.

4. The method according to claim 1, wherein the polymeric substrate material comprises celluloses, alginates, polyacrylates, polyurethanes, or polyamides.

5. The method according to claim 1, wherein the polymeric substrate comprises an anionic polymer, and said silver salt comprises a salt of $Ag^+$ with the anionic polymer.

6. The method according to claim 1, wherein the dye comprises an antioxidant dyestuff.

7. The method according to claim 6, wherein the antioxidant dyestuff comprises gentian violet, aniline blue, methylene blue, crystal violet, acriflavine, 9-aminoacridine, acridine yellow, acridine orange, proflavin, quinacrine, brilliant green, trypan blue, trypan red, malachite green, azacrine, methyl violet, methyl orange, methyl yellow, ethyl violet, acid orange, acid yellow, acid blue, acid red, thioflavin, aiphazurine, indigo blue, or methylene green.

8. The method according to claim 1, wherein the polymeric substrate consists essentially of a mixture of an oxidized cellulose with a collagen and/or a chitosan.

9. The method according to claim 1, further comprising:
sterilizing the antioxidant wound dressing material; and
packaging the wound dressing material in a microorganism-impermeable container.

10. The method according to claim 1, wherein the antioxidant wound dressing material has a free radical activity in a diphenylpicrylhydrazyl (DPPH) test for antioxidant activity of at least about 15%.

11. A wound dressing, comprising:
an antioxidant wound dressing material comprising a silver salt and an antioxidant dye; and
a backing sheet configured to be attached to the antioxidant wound dressing material to extend around edges of the antioxidant wound dressing material to form a backing sheet marginal region;
wherein the antioxidant dye is adapted to stabilize silver salts against photochemical reduction; and
the antioxidant dye is present in an amount of from about 0.2 wt. % to about 2 wt. % based on a dry weight of the antioxidant wound dressing material.

12. The wound dressing according to claim 11, wherein the antioxidant wound dressing material and the backing sheet are sterile and packaged in a microorganism-impermeable container.

13. The wound dressing according to claim 11, wherein the backing sheet is liquid impermeable.

14. The wound dressing according to claim 11, wherein the backing sheet has a thickness in a range of approximately 10 to 1,000 μmicrometers.

15. The wound dressing according to claim 11, wherein the backing sheet has a thickness in a range of approximately 100 to 500 μmicrometers.

16. The wound dressing according to claim 11, wherein the backing sheet comprises a polymer comprising polyurethanes poly alkoxyalkyl acrylates methacrylates.

17. The wound dressing according to claim 16, wherein the backing sheet comprises a continuous layer of a high density blocked polyurethane foam.

18. The wound dressing according to claim 11, further comprising an absorbent layer disposed between the antioxidant wound dressing material and the backing sheet.

19. The wound dressing according to claim 18, wherein the absorbent layer comprises gauzes, nonwoven fabrics, superabsorbents, or hydrogels.

20. The wound dressing according to claim 18, wherein the absorbent layer comprises an open-celled hydrophilic polyurethane foam.

21. The wound dressing according to claim 11, further comprising an adhesive layer disposed between the antioxidant wound dressing material and the backing sheet.

22. The wound dressing according to claim 11, wherein a removable cover sheet is disposed on a wound-facing surface of the wound dressing.

23. The wound dressing according to claim 11, wherein the backing sheet is coated with a pressure sensitive adhesive.

24. The wound dressing according to claim 11, wherein the antioxidant wound dressing material is in the form of a continuous solid sheet, a solid sheet with at least one aperture, a web, a woven fabric, a knitted fabric, a nonwoven fabric, a freeze-dried sponge or a solvent-dried sponge.

25. The wound dressing according to claim 11, wherein the antioxidant wound dressing material comprises from about 0.01 wt. % to about 5 wt. % of silver, based on a dry weight of the antioxidant wound dressing material.

26. A wound dressing, comprising:
an antioxidant wound dressing material, comprising:
a silver salt, and
a dye which stabilizes the silver salt against photochemical reduction; and
a backing sheet configured to be attached to the antioxidant wound dressing material and to extend around edges of the antioxidant wound dressing material to form a margin.

27. A wound dressing, comprising:
an antioxidant wound dressing material comprising from about 0.01 wt. % to about 5 wt. % of silver, based on a dry weight of the antioxidant wound dressing material; and
a backing sheet configured to be attached to the antioxidant wound dressing material and to extend around edges of the antioxidant wound dressing material to form a margin.

28. A wound dressing, comprising:
an antioxidant wound dressing material comprising a dye adapted to stabilize silver salts against photochemical reduction; and
a backing sheet configured to be attached to the antioxidant wound dressing material and to extend around edges of the antioxidant wound dressing material to form a margin.

29. The wound dressing of claim 28, wherein the dye is present in an amount of from about 0.2 wt. % to about 2 wt. % based on a dry weight of the antioxidant wound dressing material.

30. The wound dressing of claim 11, wherein the antioxidant dye comprises gentian violet, aniline blue, methylene blue, crystal violet, acriflavine, 9-aminoacridine, acridine yellow, acridine orange, proflavin, quinacrine, brilliant green, trypan blue, trypan red, malachite green, azacrine, methyl violet, methyl orange, methyl yellow, ethyl violet, acid orange, acid yellow, acid blue, acid red, thioflavin, alphazurine, indigo blue, or methylene green.

31. The wound dressing of claim 11, wherein the antioxidant dye has an antioxidant activity of at least about 15% in the diphenylpicrylhydrazyl (DPPH) test.

32. The wound dressing of claim 11, wherein the silver salt comprises silver oxide, silver chromate, silver allantoinate, silver borate, silver glycerolate, silver nitrate, silver acetate, silver chloride, silver sulfate, silver lactate, silver bromide, silver iodide, silver carbonate, silver citrate, silver laurate, silver deoxycholate, silver salicylate, silver p-aminobenzoate, or silver p-aminosalicylate.

33. The wound dressing of claim 26, wherein the dye comprises gentian violet, aniline blue, methylene blue, crystal violet, acriflavine, 9-aminoacridine, acridine yellow, acridine orange, proflavin, quinacrine, brilliant green, trypan blue, trypan red, malachite green, azacrine, methyl violet, methyl orange, methyl yellow, ethyl violet, acid orange, acid yellow, acid blue, acid red, thioflavin, alphazurine, indigo blue, or methylene green.

34. The wound dressing of claim 26, wherein the dye has an antioxidant activity of at least about 15% in the diphenylpicrylhydrazyl (DPPH) test.

35. The wound dressing of claim 26, wherein the silver salt comprises silver oxide, silver chromate, silver allantoinate, silver borate, silver glycerolate, silver nitrate, silver acetate, silver chloride, silver sulfate, silver lactate, silver bromide, silver iodide, silver carbonate, silver citrate, silver laurate, silver deoxycholate, silver salicylate, silver p-aminobenzoate, or silver p-aminosalicylate.

36. The wound dressing of claim 27, wherein the dye comprises gentian violet, aniline blue, methylene blue, crystal violet, acriflavine, 9-aminoacridine, acridine yellow, acridine orange, proflavin, quinacrine, brilliant green, trypan blue, trypan red, malachite green, azacrine, methyl violet, methyl orange, methyl yellow, ethyl violet, acid orange, acid yellow, acid blue, acid red, thioflavin, alphazurine, indigo blue, or methylene green.

37. The wound dressing of claim 27, wherein the dye has an antioxidant activity of at least about 15% in the diphenylpicrylhydrazyl (DPPH) test.

38. The wound dressing of claim 27, wherein the silver salt comprises silver oxide, silver chromate, silver allantoinate, silver borate, silver glycerolate, silver nitrate, silver acetate, silver chloride, silver sulfate, silver lactate, silver bromide, silver iodide, silver carbonate, silver citrate, silver laurate, silver deoxycholate, silver salicylate, silver p-aminobenzoate, or silver p-aminosalicylate.

39. The wound dressing of claim 28, wherein the dye comprises gentian violet, aniline blue, methylene blue, crystal violet, acriflavine, 9-aminoacridine, acridine yellow, acridine orange, proflavin, quinacrine, brilliant green, trypan blue, trypan red, malachite green, azacrine, methyl violet, methyl orange, methyl yellow, ethyl violet, acid orange, acid yellow, acid blue, acid red, thioflavin, alphazurine, indigo blue, or methylene green.

40. The wound dressing of claim 28, wherein the dye has an antioxidant activity of at least about 15% in the diphenylpicrylhydrazyl (DPPH) test.

41. The wound dressing of claim 28, wherein the silver salt comprises silver oxide, silver chromate, silver allantoinate, silver borate, silver glycerolate, silver nitrate, silver acetate, silver chloride, silver sulfate, silver lactate, silver bromide, silver iodide, silver carbonate, silver citrate, silver laurate, silver deoxycholate, silver salicylate, silver p-aminobenzoate, or silver p-aminosalicylate.

* * * * *